United States Patent
Thomenius et al.

(10) Patent No.: US 7,280,435 B2
(45) Date of Patent: Oct. 9, 2007

(54) SWITCHING CIRCUITRY FOR RECONFIGURABLE ARRAYS OF SENSOR ELEMENTS

(75) Inventors: Kai Erik Thomenius, Clifton Park, NY (US); Rayette Ann Fisher, Niskayuna, NY (US); Robert Gideon Wodnicki, Niskayuna, NY (US); Christopher Robert Hazard, Schenectady, NY (US); Lowell Scott Smith, Niskayuna, NY (US); David Martin Mills, Niskayuna, NY (US)

(73) Assignee: General Electric Company, Schenectady, NY (US)

(*) Notice: Subject to any disclaimer, the term of this patent is extended or adjusted under 35 U.S.C. 154(b) by 431 days.

(21) Appl. No.: 10/978,196

(22) Filed: Oct. 29, 2004

(65) Prior Publication Data
US 2005/0169107 A1    Aug. 4, 2005

Related U.S. Application Data

(63) Continuation-in-part of application No. 10/383,990, filed on Mar. 6, 2003, now Pat. No. 6,865,140.

(51) Int. Cl.
*H04R 17/00* (2006.01)
*A61B 8/00* (2006.01)

(52) U.S. Cl. ............... 367/153; 367/105; 367/181; 600/447; 600/459

(58) Field of Classification Search ........... 367/105, 367/153, 178, 181; 600/447, 459
See application file for complete search history.

(56) References Cited

U.S. PATENT DOCUMENTS 4,307,613 A    12/1981    Fox (Continued)

FOREIGN PATENT DOCUMENTS

EP    1 026 663 A2    9/2000

(Continued)

OTHER PUBLICATIONS

Ladabaum et al., Surface Micromachined Capacitive ultrasonic Transducer, IEEE Trans. Ultrasonics, Ferroelectrics and Frequency Control, vol. 45, No. 3, May 1998. pp. 678-690.

(Continued)

*Primary Examiner*—Ian J. Lobo
(74) *Attorney, Agent, or Firm*—Fletcher Yoder

(57) ABSTRACT

A device comprising an array of sensors that are reconfigurable by means of a switching network. The sensors may be optical, thermal or pressure sensors or ultrasonic transducers. More specifically, the device comprises: a multiplicity of sensor elements; a plurality of bus lines; a set of access switches for selectively connecting a set of the sensor elements in a row to a bus line, one of the access switches being connected to a first sensor element; a multiplicity of sets of matrix switches, each of the sets of matrix switches selectively connecting a respective sensor element of the multiplicity of sensor elements to a respective set of adjacent sensor elements, one of the matrix switches being connected to the first sensor element and to a second sensor element that is not a member of the set of sensor elements; and control circuitry that controls the access switches and the matrix switches in accordance with a selected switching configuration such that the first sensor element is connected to the bus line via said one access switch, while at the same time the second sensor element is connected to said one access switch via said one matrix switch.

39 Claims, 12 Drawing Sheets

U.S. PATENT DOCUMENTS

| | | |
|---|---|---|
| 4,641,660 A | 2/1987 | Bele |
| 4,890,267 A | 12/1989 | Rudolph |
| 5,146,435 A | 9/1992 | Bernstein |
| 5,452,268 A | 9/1995 | Bernstein |
| 5,558,623 A | 9/1996 | Cody |
| 5,569,968 A | 10/1996 | Lal et al. |
| 5,596,222 A | 1/1997 | Bernstein |
| 5,619,476 A | 4/1997 | Haller et al. |
| 5,684,324 A | 11/1997 | Bernstein |
| 5,732,706 A | 3/1998 | White et al. |
| 5,870,351 A | 2/1999 | Ladabaum et al. |
| 5,894,452 A | 4/1999 | Ladabaum et al. |
| 5,902,241 A | 5/1999 | Seyed-Bolorforosh et al. |
| 5,982,709 A | 11/1999 | Ladabaum et al. |
| 6,004,832 A | 12/1999 | Haller et al. |
| 6,120,449 A * | 9/2000 | Snyder et al. ............... 600/447 |
| 6,292,435 B1 | 9/2001 | Savord et al. |
| 6,320,239 B1 | 11/2001 | Eccardt et al. |
| 6,325,757 B1 | 12/2001 | Erikson et al. |
| 6,328,697 B1 | 12/2001 | Fraser |
| 6,359,367 B1 | 3/2002 | Sumanaweera et al. |
| 6,381,197 B1 | 4/2002 | Savord et al. |
| 6,384,516 B1 | 5/2002 | Fraser |
| 6,443,901 B1 | 9/2002 | Fraser |
| 6,503,204 B1 | 1/2003 | Sumanaweera et al. |
| 6,571,445 B2 | 6/2003 | Ladabaum |
| 6,585,653 B2 | 7/2003 | Miller |
| 6,589,180 B2 * | 7/2003 | Erikson et al. ............... 600/459 |
| 6,736,779 B1 | 5/2004 | Sano et al. |
| 6,865,140 B2 | 3/2005 | Thornenius et al. |
| 2002/0048219 A1 | 4/2002 | Ladabaum et al. |
| 2005/0146371 A1 * | 7/2005 | Wodnicki ............... 327/382 |

FOREIGN PATENT DOCUMENTS

| | | |
|---|---|---|
| WO | WO 00/05001 | 3/2000 |

OTHER PUBLICATIONS

Dietz et al., Wideband Annular Array Response, 1978 Ultrasonics Symp. Proc., pp. 206-211.

Bailet et al., A Computer-Controlled Transducer for Real-Time Three-Dimensional Imaging, Acoustical Imaging, vol. 18, Editors: Lee and Wade, Plenum Press, New York, 1991, pp. 543-551.

Ergun et al., Fabrication and Characterization of 1-Dimensional and 2-Dimensional CMUT Arrays etc., IEEE, 2002, pp. 2361-2367.

Orallean et al., Capacitive Micornachined Ultrasonic Transducers: Next-Generation Arrays for Acoustic Imaging, IEEE Trans. Ultrasonics, Ferroelectronics, and Freq. Control, vol. 29, No. 11, Nov. 2002, pp. 1596-1610.

Jin et al., Micromachined Capacitive Ultrasonic Immersion Transducer for Medical Imaging, Proc. 20th Annual Int'l Conf. IEEE Engineering in Medicine and Biology Society, vol. 20, No. 2, 1998, pp. 779-782.

* cited by examiner

SWITCHING CIRCUITRY FOR RECONFIGURABLE ARRAYS OF SENSOR ELEMENTS

RELATED PATENT APPLICATION

This application is a continuation-in-part of and claims priority from U.S. patent application Ser. No. 10/383,990 filed on Mar. 6, 2003 now U.S. Pat. No. 6,865,140 and entitled "Mosaic Arrays Using Micromachined Ultrasound Transducers".

STATEMENT REGARDING FEDERALLY SPONSORED RESEARCH AND DEVELOPMENT

The United States Government may have certain rights in this invention pursuant to U.S. Government Contract Number DAMD17-02-1-0181 awarded by the U.S. Army.

BACKGROUND OF THE INVENTION

This invention generally relates to reconfigurable arrays of sensors (e.g., optical, thermal, pressure, ultrasonic). In particular, the invention relates to reconfigurable micromachined ultrasonic transducer (MUT) arrays. One specific application for MUTs is in medical diagnostic ultrasound imaging systems. Another specific example is for non-destructive evaluation (NDE) of materials, such as castings, forgings, or pipelines.

Conventional ultrasound imaging systems comprise an array of ultrasonic transducers that are used to transmit an ultrasound beam and then receive the reflected beam from the object being studied. Such scanning comprises a series of measurements in which the focused ultrasonic wave is transmitted, the system switches to receive mode after a short time interval, and the reflected ultrasonic wave is received, beamformed and processed for display. Typically, transmission and reception are focused in the same direction during each measurement to acquire data from a series of points along an acoustic beam or scan line. The receiver is continuously refocused along the scan line as the reflected ultrasonic waves are received.

For ultrasound imaging, the array typically has a multiplicity of transducers arranged in one or more rows and driven with separate voltages in transmit. By selecting the time delay (or phase) and amplitude of the applied voltages, the individual transducers can be controlled to produce ultrasonic waves that combine to form a net ultrasonic wave that travels along a preferred vector direction and is focused in a selected zone along the beam.

The same principles apply when the transducer probe is employed to receive the reflected sound in a receive mode. The voltages produced at the receiving transducers are summed so that the net signal is indicative of the ultrasound reflected from a single focal zone in the object. As with the transmission mode, this focused reception of the ultrasonic energy is achieved by imparting separate time delay (and/or phase shifts) and gains to the signal from each receiving transducer. The time delays are adjusted with increasing depth of the returned signal to provide dynamic focusing on receive.

The quality or resolution of the image formed is partly a function of the number of transducers that respectively constitute the transmit and receive apertures of the transducer array. Accordingly, to achieve high image quality, a large number of transducers is desirable for both two- and three-dimensional imaging applications. The ultrasound transducers are typically located in a hand-held transducer probe that is connected by a flexible cable to an electronics unit that processes the transducer signals and generates ultrasound images. The transducer probe may carry both ultrasound transmit circuitry and ultrasound receive circuitry.

A reconfigurable ultrasound array is one that allows groups of subelements to be connected together dynamically so that the shape of the resulting element can be made to match the shape of the wave front. This can lead to improved performance and/or reduced channel count. Reconfigurability can be achieved using a switching network.

Recently semiconductor processes have been used to manufacture ultrasonic transducers of a type known as micromachined ultrasonic transducers (MUTs), which may be of the capacitive (MUT) or piezoelectric (pMUT) variety. MUTs are tiny diaphragm-like devices with electrodes that convert the sound vibration of a received ultrasound signal into a modulated capacitance. For transmission the capacitive charge is modulated to vibrate the diaphragm of the device and thereby transmit a sound wave. One advantage of MUTs is that they can be made using semiconductor fabrication processes, such as microfabrication processes grouped under the heading "micromachining". The systems resulting from such micromachining processes are typically referred to as "micromachined electro-mechanical systems (MEMS).

The cMUTs are usually hexagonal-shaped structures that have a membrane stretched across them. This membrane is held close to the substrate surface by an applied bias voltage. By applying an oscillatory signal to the already biased cMUT, the membrane can be made to vibrate, thus allowing it to radiate acoustical energy. Likewise, when acoustic waves are incident on the membrane the resulting vibrations can be detected as voltage changes on the cMUT. A cMUT cell is the term used to describe a single one of these hexagonal "drum" structures. The cMUT cells can be very small structures. Typical cell dimensions are 25–50 microns from flat edge to flat edge on the hexagon. The dimensions of the cells are in many ways dictated by the designed acoustical response. It may not be possible to create larger cells that still perform well in terms of frequency response and sensitivity desired.

Unfortunately, it is difficult to produce electronics that would allow individual control over such small cells. While in terms of the acoustical performance of the array as a whole, the small cell size is excellent and leads to great flexibility, control is limited to larger structures. Grouping together multiple cells and connecting them electrically allows one to create a larger subelement, which can have the individual control while maintaining the desired acoustical response. So a subelement is a group of electrically connected cells that cannot be reconfigured. For the purpose of this disclosure, the subelement is the smallest independently controlled acoustical unit. One can form rings or elements by connecting subelements together using a switching network. The elements can be reconfigured by changing the state of the switching network. However, subelements comprise connected cells that are not switchably disconnectable and thus cannot be reconfigured. All of the following analysis is also valid if the array is made of PZT or some other more common or future transducer technology.

Reconfigurability using silicon-based ultrasound transducer subelements was described in U.S. patent application Ser. No. 10/383,990. One form of reconfigurability is the mosaic annular array, also described in that patent application. The mosaic annular array concept involves building annular elements by grouping subelements together using a reconfigurable electronic switching network. The goal is to reduce the number of beamforming channels, while maintaining image quality and improving slice thickness. To reduce system channels, the mosaic annular array makes use of the fact that for an unsteered beam, the delay contours on the surface of the underlying two-dimensional transducer array are circular. In other words, the iso-delay curves are annuli about the center of the beam. The circular symmetry of the delays leads to the obvious grouping of those subelements with common delays and leads to the annular array concept. The reconfigurability can be used to step the beam along the larger underlying two-dimensional transducer array in order to form a scan or image. The reconfigurability might also be used to improve performance for multiple transmit applications by assigning more channels to the smaller active aperture in the near field. There are many other applications where reconfigurability might prove useful.

Reconfigurable ultrasound arrays require a complex switching network that may be difficult or impossible to implement with currently available electronics. There is a need for a simplified switching network that provides acceptable performance.

BRIEF DESCRIPTION OF THE INVENTION

The invention is directed to a device comprising an array of sensors that are reconfigurable by means of a switching network. The sensors may be optical, thermal or pressure sensors or ultrasonic transducers. The embodiment disclosed herein uses a two-dimensional array of capacitive micromachined ultrasound transducers (cMUTs) as the underlying grid from which larger elements are constructed. The present invention is not limited, however, to cMUT structures and is equally applicable to other conventional or future transducer technologies.

One aspect of the invention is a device comprising: a multiplicity of sensor elements; a plurality of bus lines; a first set of access switches for selectively connecting a first set of the sensor elements in a first row to a first bus line of the plurality of bus lines, a first access switch of the first set of access switches being connected to a first sensor element that is a member of the first set of sensor elements; a multiplicity of sets of matrix switches, each of the sets of matrix switches selectively connecting a respective sensor element of the multiplicity of sensor elements to a respective set of adjacent sensor elements, a first matrix switch of the multiplicity of sets of matrix switches being connected to the first sensor element and to a second sensor element that is not a member of the first set of sensor elements; and control circuitry that controls the access switches and the matrix switches in accordance with a selected switching configuration such that the first sensor element is connected to the first bus line via the first access switch, while at the same time the second sensor element is connected to the first access switch via the first matrix switch.

Another aspect of the invention is device comprising: a multiplicity of sensor elements arranged in rows; a plurality of bus lines; a plurality of system channels; a multiplicity of switches for selectively connecting various bus lines to various system channels; a first set of access switches for selectively connecting a first set of the sensor elements in a first row to a first bus line of the plurality of bus lines, each access switch of the first set of access switches being disposed underneath a respective sensor element of the first set of sensor elements, a first access switch of the first set of access switches being connected to a first sensor element that is a member of the first set of sensor elements; a multiplicity of sets of matrix switches, each of the sets of matrix switches selectively connecting a respective sensor element of the multiplicity of sensor elements to a respective set of adjacent sensor elements, a first matrix switch of the multiplicity of sets of matrix switches being connected to the first sensor element and to a second sensor element that is not a member of the first set of sensor elements; and control circuitry that controls the multiplexer switches, the access switches and the matrix switches in accordance with a selected switching configuration such that the first sensor element is connected to a first system channel via a first cross-point switch of the multiplicity of cross-point switches that is connected to the first bus line, via the first bus line, and via the first access switch, while at the same time the second sensor element is connected to the first access switch via the first matrix switch.

A further aspect of the invention is an ultrasound transducer array comprising: a multiplicity of bus lines; a multiplicity of access switches, each access switch being connected to one of the bus lines; and a multiplicity of subelements, each subelement being switchably connectable to one of the bus lines via a respective one of the access switches and comprising a respective multiplicity of MUT cells and a respective plurality of matrix switches, and each MUT cell within a particular subelement being connected together and not switchably disconnectable, wherein each subelement is switchably connectable to each adjacent subelement via a respective matrix switch.

Other aspects of the invention are disclosed and claimed below.

BRIEF DESCRIPTION OF THE DRAWINGS

Reference will now be made to the drawings in which similar elements in different drawings bear the same reference numerals.

DETAILED DESCRIPTION OF THE INVENTION

The invention is directed to a device comprising an array of sensors that are reconfigurable by means of a switching network. For the purposes of illustration, the reconfigurable array will be described with reference to capacitive micromachined ultrasonic transducers (cMUTs). However, it should be understood that the aspects of the invention disclosed herein are not limited in their application to probes employing cMUTs, but rather may also be applied to probes that employ pMUTs or even diced piezoceramic arrays where each of the diced subelements are connected by interconnect means to an underlying switching layer. The same aspects of the invention also have application in reconfigurable arrays of optical, thermal or pressure sensors.

Figure 1:
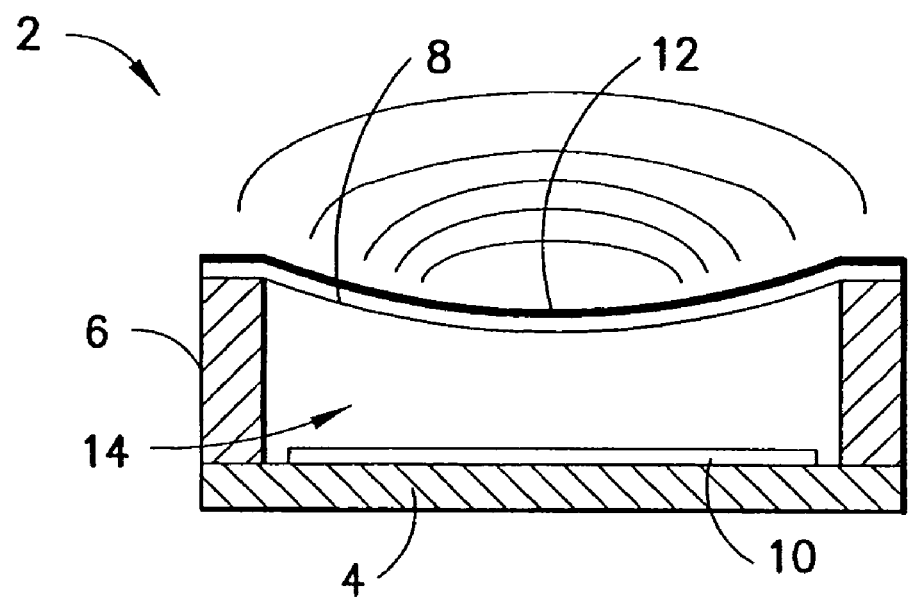
FIG. 1 is a drawing showing a cross-sectional view of a typical cMUT cell.

Referring to FIG. 1, a typical cMUT transducer cell 2 is shown in cross section. An array of such cMUT transducer cells is typically fabricated on a substrate 4, such as a heavily doped silicon (hence, semiconductive) wafer. For each cMUT transducer cell, a thin membrane or diaphragm 8, which may be made of silicon nitride, is suspended above the substrate 4. The membrane 8 is supported on its periphery by an insulating support 6, which may be made of silicon oxide or silicon nitride. The cavity 14 between the membrane 8 and the substrate 4 may be air- or gas-filled or wholly or partially evacuated. Typically, cMUTs are evacuated as completely as the processes allow. A film or layer of conductive material, such as aluminum alloy or other suitable conductive material, forms an electrode 12 on the membrane 8, and another film or layer made of conductive material forms an electrode 10 on the substrate 4. Alternatively, the bottom electrode can be formed by appropriate doping of the semiconductive substrate 4.

The two electrodes 10 and 12, separated by the cavity 14, form a capacitance. When an impinging acoustic signal causes the membrane 8 to vibrate, the variation in the capacitance can be detected using associated electronics (not shown in FIG. 1), thereby transducing the acoustic signal into an electrical signal. Conversely, an AC signal applied to one of the electrodes will modulate the charge on the electrode, which in turn causes a modulation in the capacitive force between the electrodes, the latter causing the diaphragm to move and thereby transmit an acoustic signal.

The individual cells can have round, rectangular, hexagonal, or other peripheral shapes. Hexagonal shapes provide dense packing of the cMUT cells of a transducer subelement. The cMUT cells can have different dimensions so that the transducer subelement will have composite characteristics of the different cell sizes, giving the transducer a broadband characteristic.

Unfortunately, it is difficult to produce electronics that would allow individual control over such small cells. While in terms of the acoustical performance of the array as a whole, the small cell size is excellent and leads to great flexibility, control is limited to larger structures. Grouping together multiple cells and connecting them electrically allows one to create a larger subelement, which can have the individual control while maintaining the desired acoustical response. One can form rings or elements by connecting subelements together using a switching network. The elements can be reconfigured by changing the state of the switching network. However, individual subelements cannot be reconfigured to form different subelements.

MUT cells can be connected together (i.e., without intervening switches) in the micromachining process to form subelements. The term "acoustical subelement" will be used in the following to describe such a cluster. These acoustical subelements will be interconnected by microelectronic switches to form larger elements by placing such switches within the silicon layer or on a different substrate situated directly adjacent to the transducer array.

As used herein, the term "acoustical subelement" is a single cell or a group of electrically connected cells that cannot be reconfigured, i.e., the subelement is the smallest independently controlled acoustical unit. The term "subelement" means an acoustical subelement and its associated integrated electronics. An "element" is formed by connecting subelements together using a switching network. The elements can be reconfigured by changing the state of the switching network. At least some of the switches included in the switching network are part of the "associated integrated electronics", as explained in greater detail below.

Figure 2:
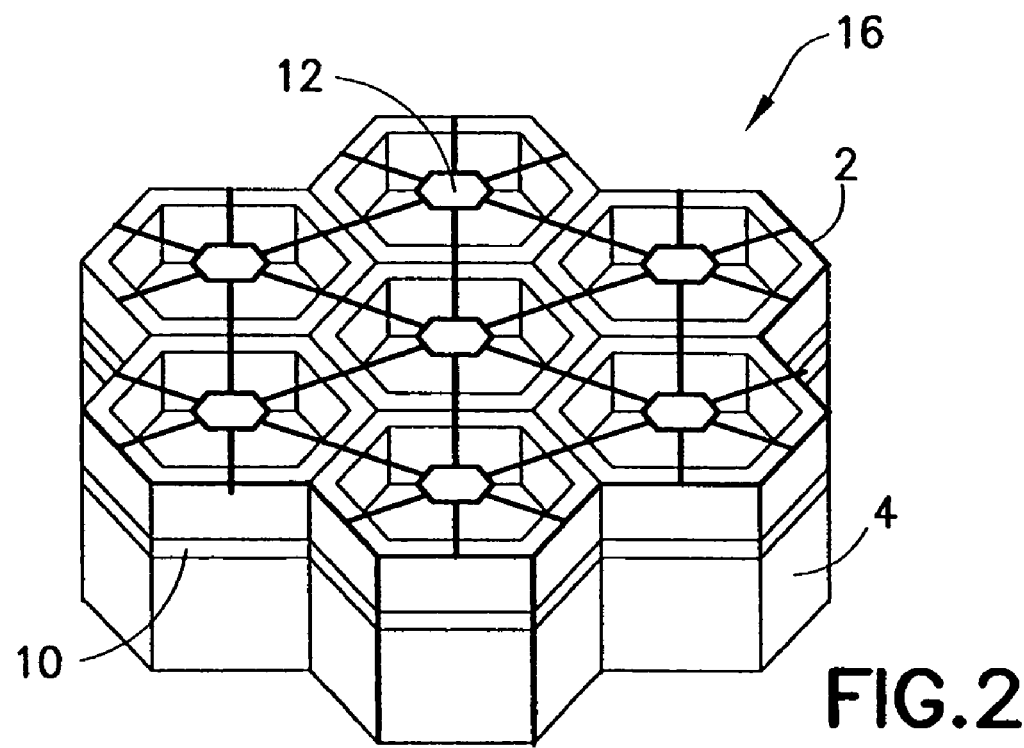
FIG. 2 is a drawing showing a "daisy" subelement formed from seven hexagonal MUT cells having their top and bottom electrodes respectively connected together without intervening switches. This drawing is taken from U.S. patent application Ser. No. 10/383,990.

For the purpose of illustration, FIG. 2 shows a "daisy" transducer subelement 16 made up of seven hexagonal cMUT cells 2: a central cell surrounded by a ring of six cells, each cell in the ring being contiguous with a respective side of the central cell and the adjoining cells in the ring. The top electrodes 12 of each cMUT cell 2 are electrically coupled together by connections that are not switchably disconnectable. In the case of a hexagonal array, six conductors radiate outward from the top electrode 12 and are respectively connected to the top electrodes of the neighboring cMUT cells (except in the case of cells on the periphery, which connect to three, not six, other cells). Similarly, the bottom electrodes 10 of each cell 2 are electrically coupled together by connections that are not switchably disconnectable, forming a seven-times-larger capacitive transducer subelement 16.

Subelements of the type seen in FIG. 2 can be arranged to form a two-dimensional array on a semiconductive (e.g., silicon) substrate. These subelements can be reconfigured to form elements, such as annular rings, using a switching network. Reconfigurability using silicon-based ultrasound transducer subelements was described in U.S. patent application Ser. No. 10/383,990. One form of reconfigurability is the mosaic annular array, also described in that patent application. The mosaic annular array concept involves building annular elements by grouping subelements together using a reconfigurable electronic switching network. The goal is to reduce the number of beamforming channels, while maintaining image quality and improving slice thickness. To reduce system channels, the mosaic annular array makes use of the fact that for an unsteered beam, the delay contours on the surface of the underlying two-dimensional transducer array are circular. In other words, the iso-delay curves are annuli about the center of the beam. The circular symmetry of the delays leads to the obvious grouping of those subelements with common delays. The reconfigurability can be used to step the beam along the larger underlying two-dimensional transducer array in order to form a scan or image.

Figure 3:
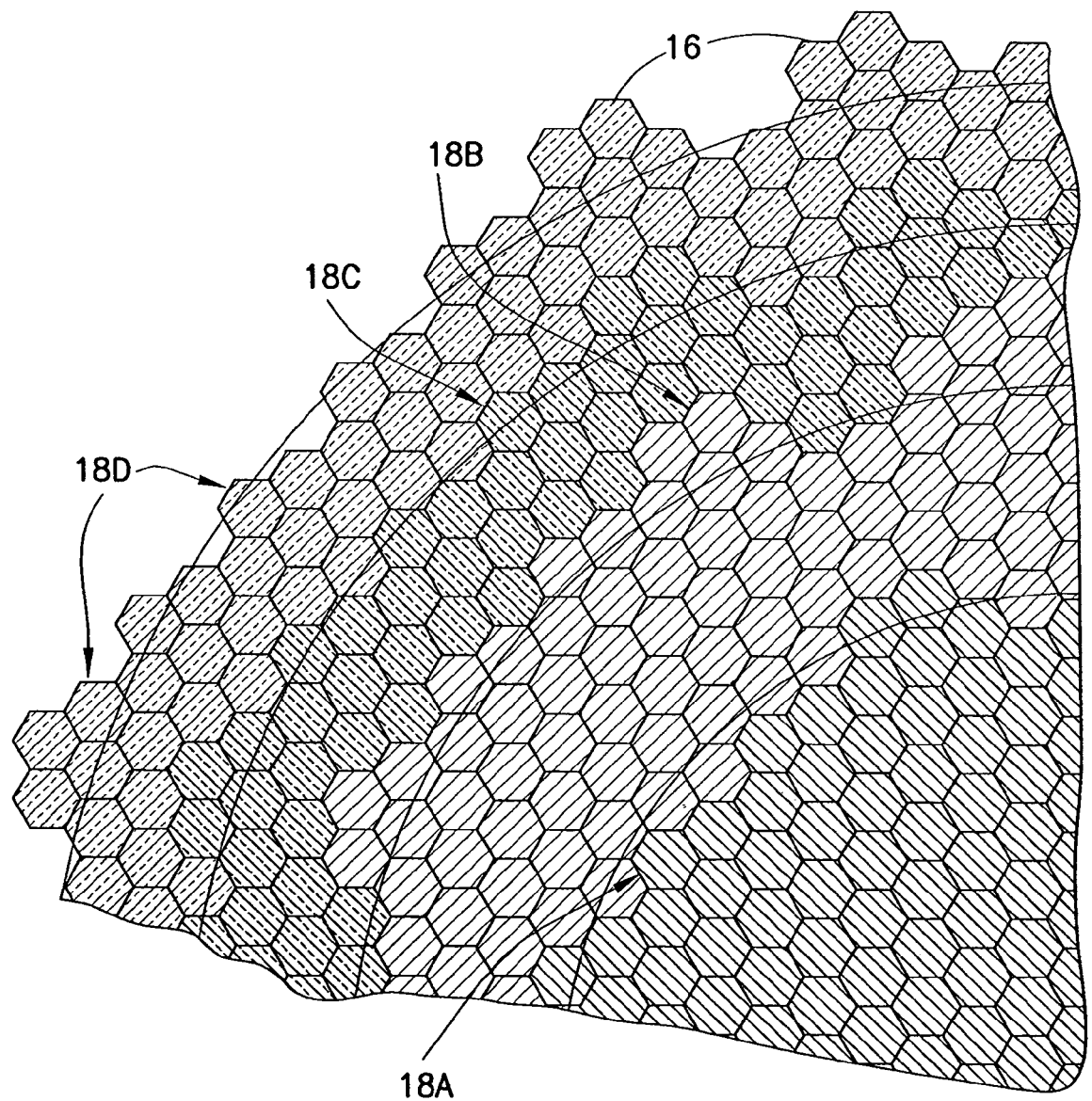
FIG. 3 is a drawing showing a sector of a mosaic array comprising four annular elements as disclosed in U.S. patent application Ser. No. 10/383,990, each element consisting of a tessellation of "daisy" subelements configured to have approximately equal area per element.

There are numerous ways in which one can form transducer arrays using MUT cells and acoustical subelements. FIG. 3 shows one example of tessellations of acoustical subelements to form a mosaic array. In the embodiment shown in FIG. 3, four approximately annular elements (referenced by numerals 18A–D respectively), each comprising a tessellation of "daisy" acoustical subelements (seven MUT cells connected together per subelement), are configured to have approximately equal area per element. The tessellation in each case can be made up of multiple subelement types. The array pattern need not be a tessellation, but can have areas without acoustical subelements. For instance, there could be vias to bring top electrode connections of the acoustical subelement or cells below the array.

The subelement configurations can be changed to optimize various acoustic parameters such as beamwidth, side lobe level, or depth of focus. Alternatively, the acoustical subelements could be grouped to form one aperture for the transmit operation and immediately switched to another aperture for the receive portion. While FIG. 3 shows respective portions of approximately annular elements, other configurations can be implemented, for example, non-continuous rings, octal rings, or arcs. The choice of pattern will depend on the application needs.

Most apertures will consist of contiguous grouped subelements interconnected to form a single larger element, such as the annular elements shown in FIG. 3. In this case, it is not necessary to connect every subelement directly to its respective bus line. It is sufficient to connect a limited number of subelements within a given group and then connect the remaining subelements to each other. In this way the transmit signal is propagated from the system along the bus lines and into the element along a limited number of access points. From there the signal spreads within the element through local connections.

Given a particular geometry, the reconfigurable array maps acoustical subelements to system channels. This mapping is designed to provide improved performance. The mapping is done through a switching network, which is ideally placed directly in the substrate upon which the cMUT cells are constructed, but can also be in a different substrate integrated adjacent to the transducer substrate. Since cMUT arrays are built directly on top of a silicon substrate, the switching electronics can be incorporated into that substrate. For a PZT or more conventional implementation, the switch network would simply be fabricated in a separate silicon substrate and attached to the PZT array.

Figure 4:
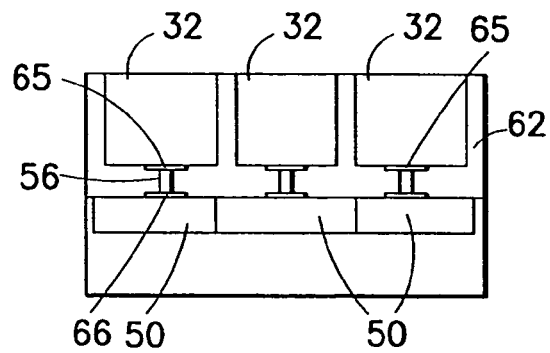
FIG. 4 is a drawing showing a cross-sectional view of a co-integrated cMUT and application specific integrated circuit (ASIC) array.

A cross-sectional view of a co-integrated cMUT and ASIC array is shown in FIG. 4 to illustrate how the connections would be made from the ASIC to the cMUTs. As shown, a single via 56 is used to connect each cMUT subelement 32 to its counterpart CMOS subelement (or "cell") 50. The vias 56, which connect the signal electrodes to respective conductive pads 66 formed on the switch ASIC, may be embedded in an acoustic backing layer 62.

Figure 5:
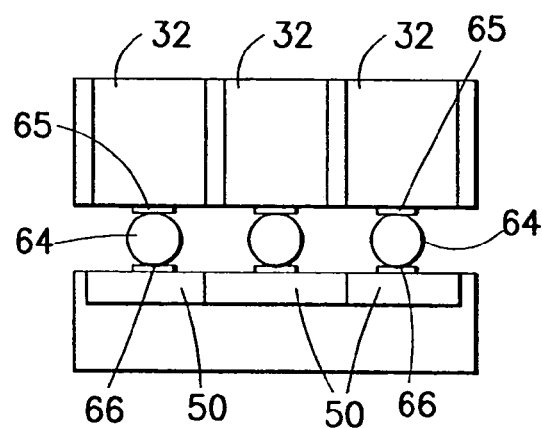
FIG. 5 is a drawing showing a cross-sectional view of a cMUT wafer connected to an ASIC switch matrix.

It is also possible to build the cMUTs on a separate wafer and connect them to the ASIC switch matrix separately, as shown in FIG. 5. Here for example, solder bumps 64 and conductive pads 66 are used to connect the individual cMUT subelements 32 to their switch electronics counterparts 50. Other packaging techniques such as Anisotropic Conductive Film (ACF) or flexible interconnect could also be used.

Figure 6:
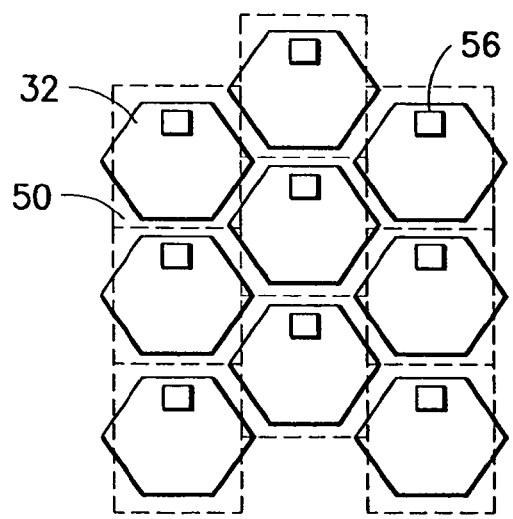
FIG. 6 is a drawing showing a top view of a hexagonal array of cMUT subelements atop a hexagonal array of associated unit switch cells.
Figure 7:
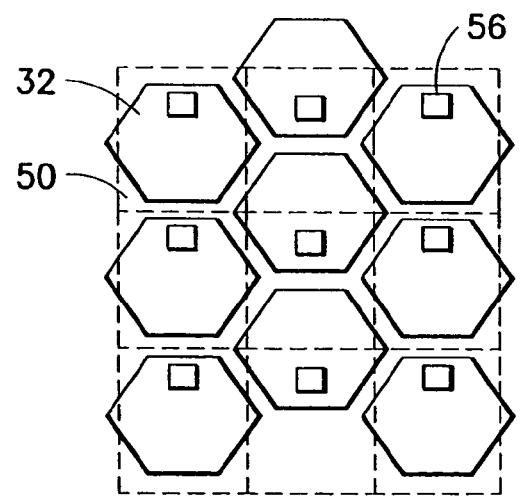
FIG. 7 is a drawing showing a top view of a hexagonal array of cMUT subelements atop a rectangular array of associated unit switch cells.

For optimum packing density it is useful to tile the cMUT subelements 32 and the associated electronics on a hexagonal grid as illustrated in FIG. 6, which shows a top view of the ASIC switch matrix. Here the CMOS unit switch cells 50 are disposed in columns where every second column is offset by half a cell height. With proper choice of the cell dimensions, this will yield a perfect hexagonal array of pads 66 as shown. The vias 56 (also arranged in a hexagonal array) then connect to the respective pads (not shown in FIG. 4) that form the basis of connections to the transducer layer above, comprising a hexagonal array of subelements. A more straightforward ASIC implementation is illustrated in FIG. 7. Here the CMOS unit switch cells 50 are arranged in horizontal rows and vertical columns to form a rectangular grid, while the hexagonal subelements 32 above them form a hexagonal grid. As shown in FIG. 7, the unit switch cell pads 66, arranged in rows and columns to form a rectangular array, still line up correctly to produce the connections such that the unit switch cells 50 are electrically connected to respective hexagonal subelements 32. In either case, the hexagonal grid pattern of the subelements makes it possible to realize the mosaic annular array beam patterns as shown in FIG. 3.

Figure 8:
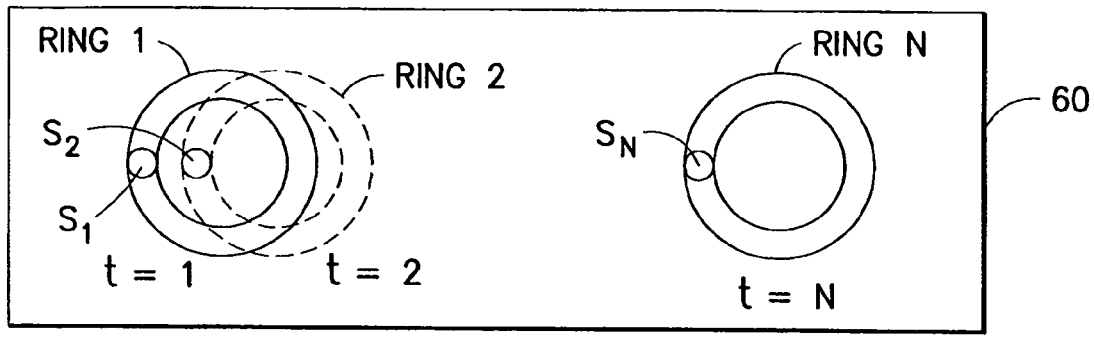
FIG. 8 is a drawing showing translation of an annular transducer element across an array.

In typical operation, the reconfigurable array is programmed with an initial aperture pattern similar to the one shown in FIG. 3. This pattern allows the beamformer to create a beam in front of the array. During imaging, the aperture is scanned across the array 60 as illustrated in FIG. 8, where the ring goes from ring 1 at t=1 to ring 2 at t=2 and finally ring N at t=N, where t is time and N is a positive integer greater than 2. In this way the beam is swept in space in front of the array and the beamformed echoes are used to build up successive lines of the image. The purpose of a reconfigurable array is to be able to accomplish the imaging operation illustrated in FIG. 8 electronically for an arbitrarily complex array pattern. Previous ultrasound scanners are capable of accomplishing electronic scanning but are limited in the complexity of the aperture due to lack of fine distribution of sensor subelements in the elevation direction and fixed geometry.

A fully reconfigurable array as illustrated in FIG. 8 presents a number of significant challenges in implementation. The sensor array is subdivided into tens of thousands of subelements. Beam patterns are built up by grouping the subelements in their connections to a finite number of system transmit/receive and beamforming channels. When used to implement the mosaic annular array concept, the reconfigurable array will form multiple rings that are translated across the array electronically. At each new step in the translation, the entire ring pattern is reprogrammed into the array to create a new configuration. One could also provide the ability to update ring patterns between transmit and receive and at multiple intervals during receive to reduce the distortion of the beam as formed, thereby improving the image quality.

In typical systems, 128 or more beamforming channels are used. Current ultrasound systems use multiplexing architectures that can route the 128 system channels to a fixed number of transducer elements. Using judicious design of these multiplexer networks, it is possible to create a standard scanning pattern with a limited amount of electronics. In most cases however, the scanning pattern is fixed and not reconfigurable due to the limitations of the network. A fully reconfigurable array does not suffer from these limitations; however, it requires a very dense switching matrix to implement it.

As is illustrated in FIG. 8, the fundamental nature of the reconfigurable array requires that any subelement can be arbitrarily connected to any system channel. For example, as the aperture is scanned from the first location to the next location, the subelement S2 first must be part of an internal ring (not shown) and then must be part of ring 2. This means that it must switch from being connected to a first system channel to being connected to a different system channel in a short period of time. This is generally true of a large number of subelements in the array during scanning operation.

Figure 9:
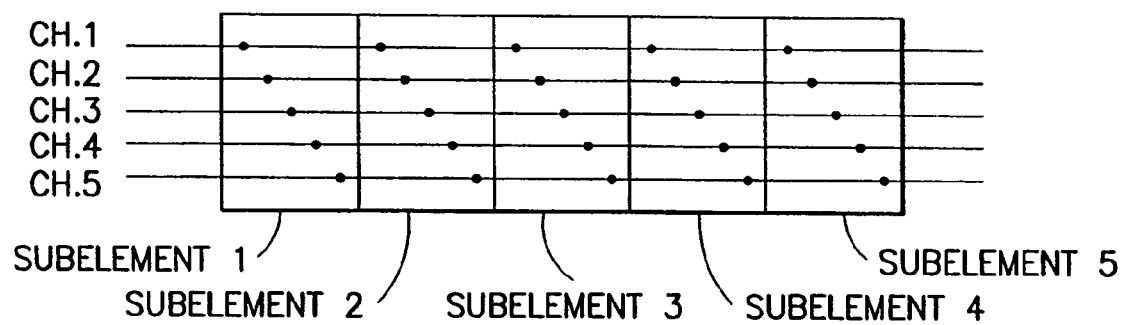
FIG. 9 is a drawing showing an architecture wherein all system channels are distributed throughout the array such that each transducer subelement has access to every system channel.

The simplest way to implement this requirement would be to distribute all system channels throughout the array such that each subelement has access to every system channel. This architecture is illustrated in FIG. 9. Here only five system channels are shown for illustration. Each system channel is bussed through every subelement with local switches used to select which system channel is picked up by which subelement.

In a system where the matrix electronics lie directly behind the transducer array, the space for each subelement's switching electronics is reduced to the size of the subelement. In typical ultrasound systems this size is on the order of a few hundred microns but could be smaller than this. Since the size of a switch varies inversely with its on resistance, one is faced with a tradeoff: more switches with higher on resistance or fewer switches with lower on resistance. Even taking the extreme case however, in which the switches are as small as they can be, it soon becomes apparent that with present semiconductor technologies, many more than 16 switches cannot fit readily in the allotted space. Since for a real array the fully populated architecture of FIG. 9 will contain still more switches, it appears to be intractable with the current state of the art.

Although future technologies may make it quite feasible to integrate many more switches in the same space, progress in ultrasound will tend to reduce the allotted cell size since it is related to the wavelength of the imager, which must shrink for improved image quality. In addition, many more components, such as digital control and transmit/receive circuits, will migrate into this same limited area. Therefore, the fully populated architecture, while attractive for its simplicity, is not immediately tenable or practicable.

Figure 10:
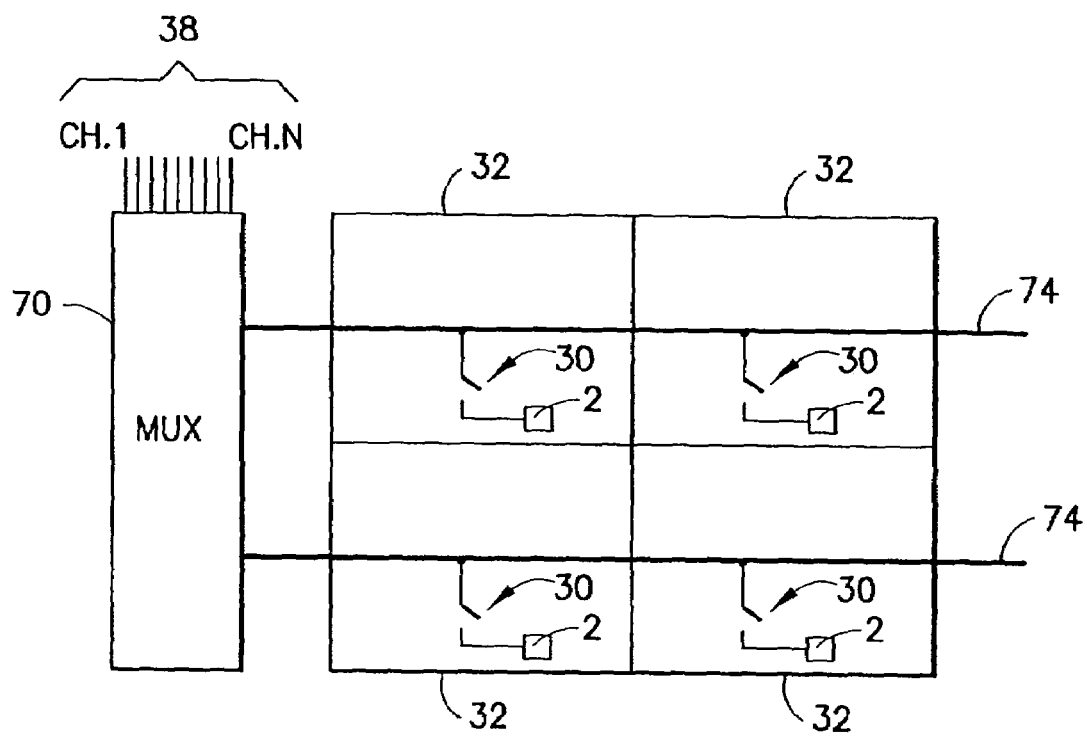
FIG. 10 is a drawing showing an architecture wherein the number of switches in each subelement is limited by having one bus line per row of subelements, the bus lines being connected to system channels via a multiplexer.
Figure 11:
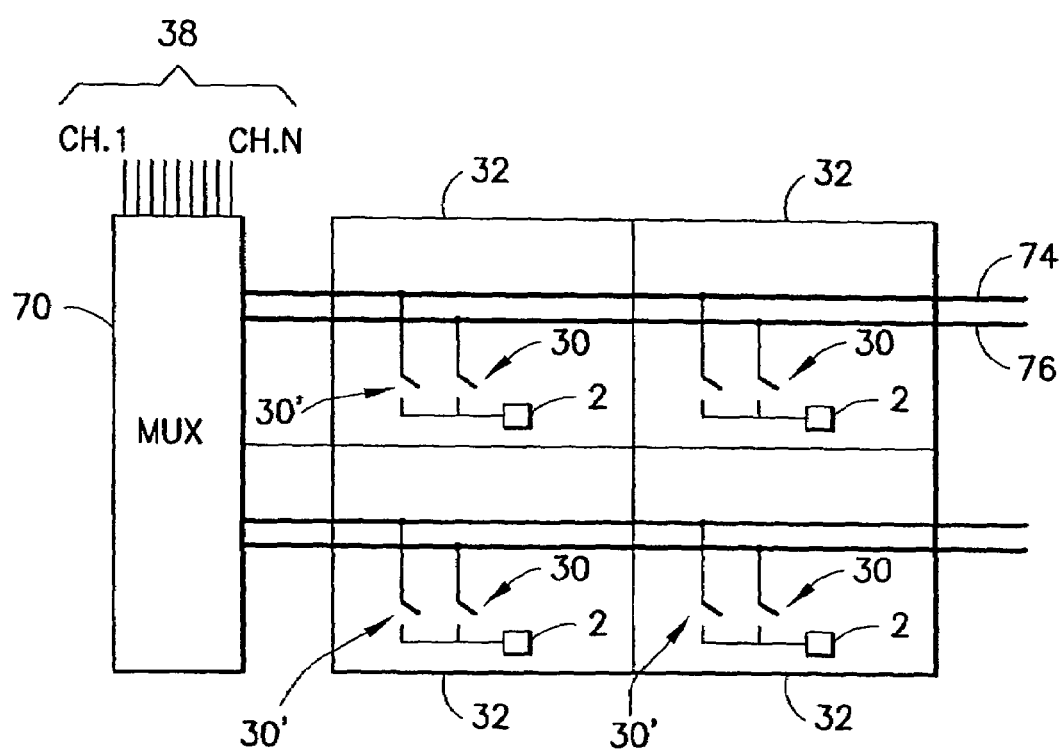
FIG. 11 is a drawing showing an architecture having multiple bus lines per row of subelements, making it possible to group subelements on different system channels within the same row.

A better solution to the interconnect problem described above is to limit the number of switches in each subelement while at the same time providing for the flexibility required in a reconfigurable array. This can be done by using a limited number of bus lines and making these reconfigurable, as is illustrated in FIG. 10. Here a multiplexer 70 is used to arbitrarily select any of the system channels 38 (CH. 1 through CH. N) to be connected to any of the bus lines 74, with each row of subelements 32 served by only a single bus line. The cMUT cells 2 of each subelement (only one cMUT cell is shown for each subelement) are connected to a bus line by means of a respective access switch 30. A key feature of this architecture is that many of the switches are located outside of the array and therefore are not constrained by the geometry of the transducers. A one-dimensional pattern can be scanned across the array using this architecture by successively selecting which row of subelements is connected to which system channel. A further improvement to this architecture is shown in FIG. 11. Here multiple bus lines 74, 76 are routed down each row of subelements 32. The cMUT cells 2 of each subelement 32 can be connected to either bus line 74 via access switch 30' or bus line 76 via access switch 30. This architecture provides flexibility in the horizontal direction since it is now possible to group elements on different system channels within the same row.

Figure 12:
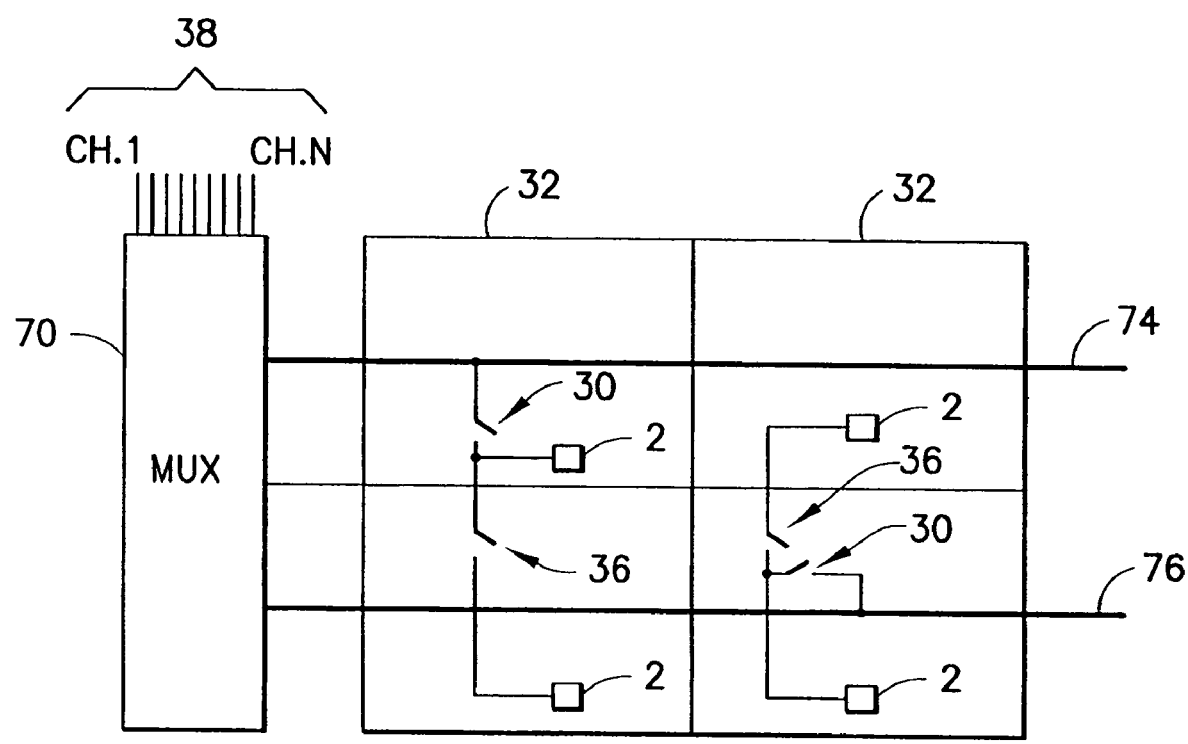
FIG. 12 is a drawing showing an architecture in accordance with one embodiment of the invention that allows a subelement in a first row to connect to a bus line for a second row of subelements by connecting to an access switch of an adjacent subelement in the second row via a matrix switch of the subelement in the first row.

A further improvement to the above architecture can be made by realizing that most apertures will consist of contiguous grouped subelements interconnected to form a single larger element. In this case, it is not necessary to connect every subelement directly to its respective bus line. It is sufficient to connect a limited number of subelements within a given group and then connect the remaining subelements to each other. In this way the transmit signal is propagated from the system along the bus lines and into the element along a limited number of access points. From there the signal spreads within the element through local connections. This architecture is illustrated in FIG. 12. Here individual subelements 32 are able to connect to the bus line associated with their row by way of access switches 30 and are able to connect to the bus line associated with an adjacent row by way of matrix switches 36, which connect one subelement to an adjacent subelement.

Figure 13:
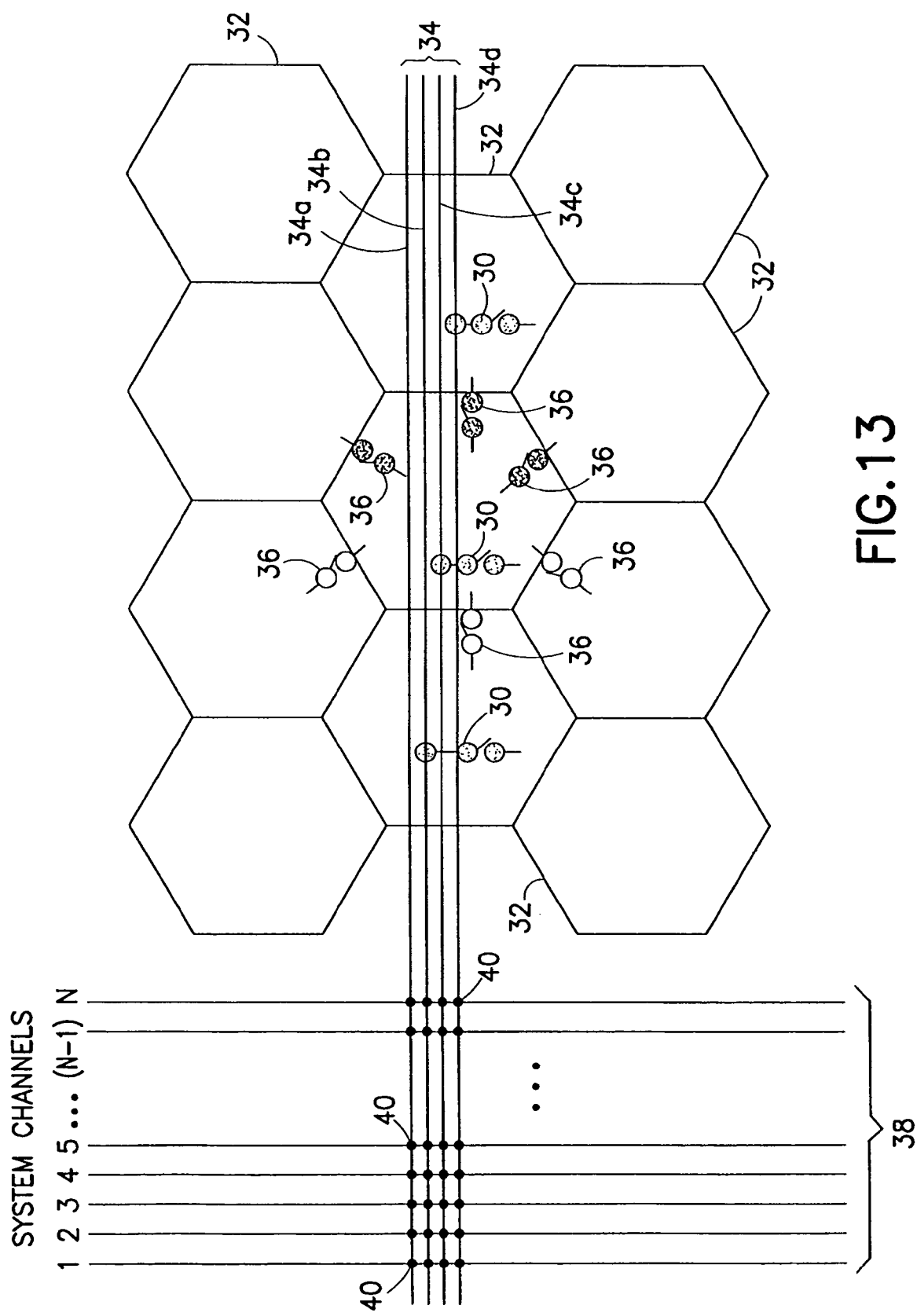
FIG. 13 is a drawing showing an architecture in accordance with another embodiment of the invention that allows a particular subelement in a particular row of a cMUT array to be connected to any one of a multiplicity of system channel bus lines.

One embodiment of the invention, shown in FIG. 13, incorporates all of the above-mentioned improvements together. Here an access switch 30 is used to connect a given subelement 32 to a row bus line of bus 34. This architecture is directly applicable to a mosaic annular array. In such a device multiple rings can be formed using the present architecture, wherein each ring is connected to a single system channel using one or more access switches, each of which is connected to a bus line, which is in turn connected to a system channel.

The access switches are staggered as shown in FIG. 13 to reduce the number required for a given number of bus lines, as discussed further below. Random ordering of access switches to bus lines (not shown) could also be employed to reduce artifacts due to the repeating patterns. More than one access switch in each subelement could be used to improve the flexibility of the array. In such an architecture, a tradeoff between flexibility and number of access switches per subelement would be made where the number is still significantly fewer than the number of bus lines and system channels. It is also possible to use more than one access switch per bus line in each element. This would improve the yield of the device since non-functioning access switches could be bypassed using the redundant access switches.

The row bus lines are connected to the system channels using a cross-point switching matrix as shown in FIG. 13. A sparse cross-point switch could be used as well in which fewer multiplexer switches would be required. Such an architecture would be more efficient in use of space but would require judicious choice of switch configurations to ensure that all bus lines could be properly connected. As shown in FIG. 12, multiple bus lines can be used per row. More bus lines improves flexibility of the array at the expense of more multiplexer switches and more routing area inside the array. It is possible to skip rows or to use different numbers of bus lines on different rows. For example, to conserve area it might be advantageous to share a group of bus lines between every pair of adjacent rows of subelements.

Figure 14:
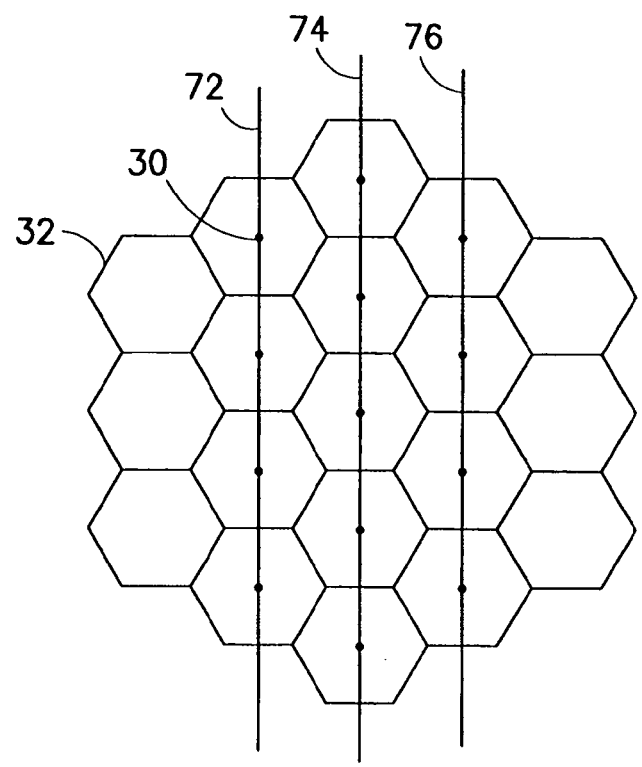
FIG. 14 is a drawing showing a hexagonal array of subelements with bus lines connected to respective columns of subelements via access switches (indicated by solid dots).
Figure 15:
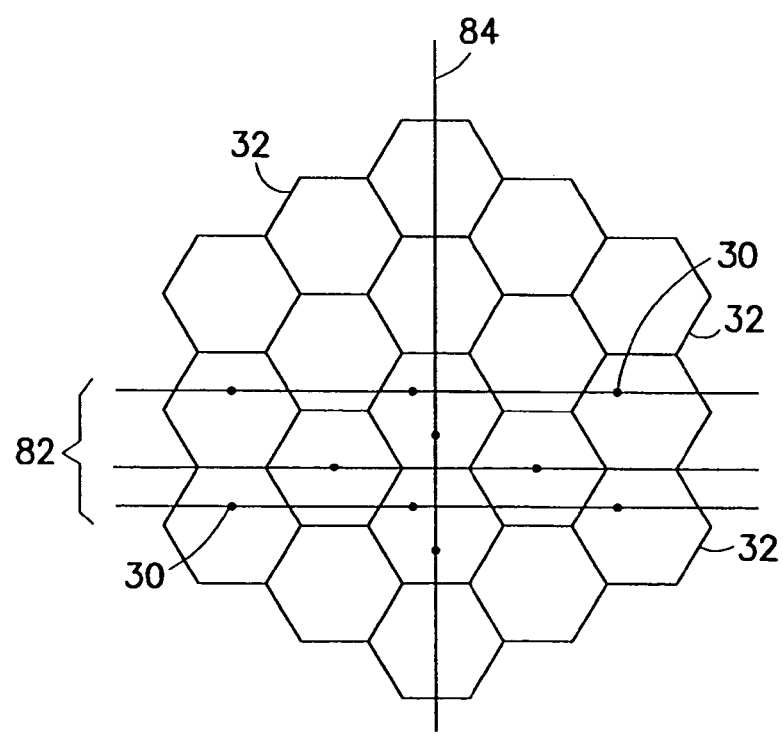
FIG. 15 is a drawing showing a hexagonal array of subelements with some subelements connected to vertical and horizontal bus lines via respective access switches (indicated by solid dots).
Figure 16:
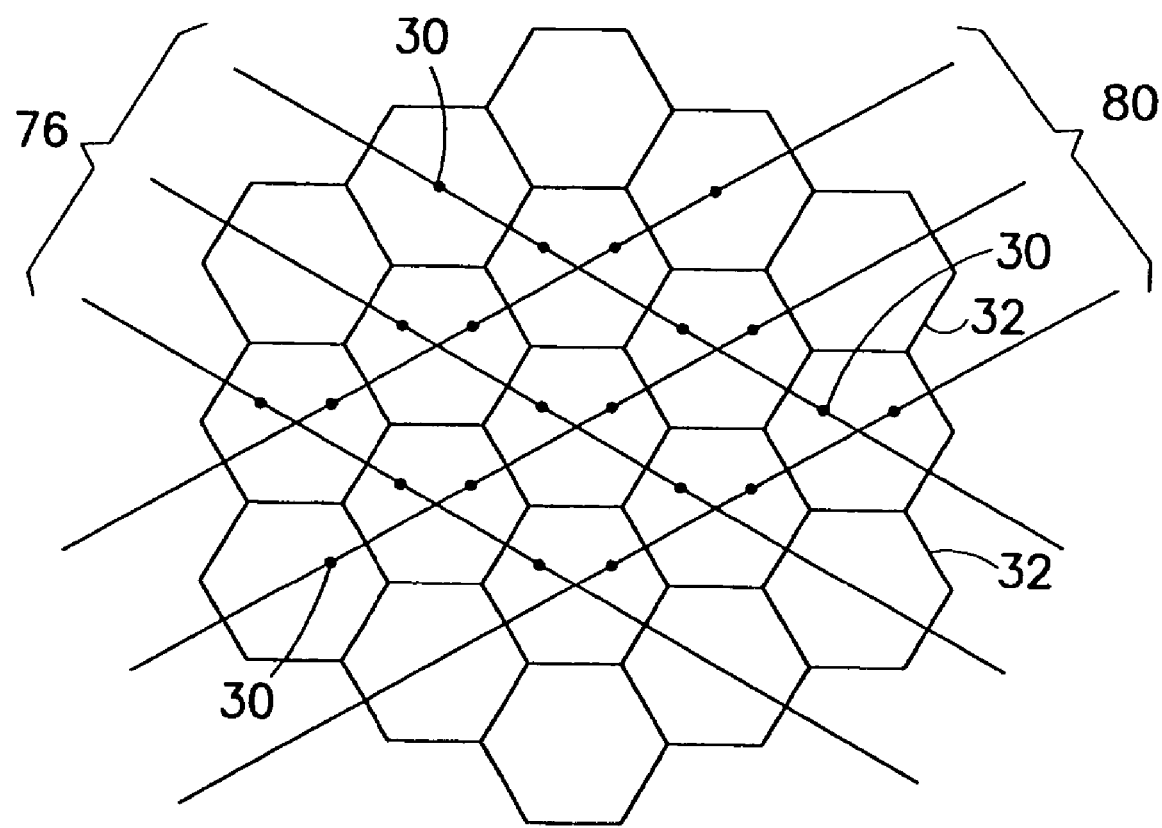
FIG. 16 is a drawing showing a hexagonal array of subelements with bus lines disposed diagonally along the natural axes of the hexagonal array. Access switches are indicated by solid dots.

Although only horizontal bus lines have been discussed thus far, it is also possible to dispose both vertically and horizontally running bus lines within an array. Bus lines could be disposed vertically as illustrated in FIG. 14 (see bus lines 72, 74, 76). Referring to FIG. 15, one set of bus lines 82 could be disposed horizontally and another set 84 disposed vertically. In this case each subelement or group of subelements will be connectable to a vertical bus line via one access switch and will further be connectable to a horizontal bus line via a different access switch. However, in the case where bus lines are run in both directions because the electronic real estate available for bus lines is running low and more bus lines are needed, but there is still only a single access switch in a subelement, then each subelement's access switch could be connected to either the horizontal bus line or the vertical bus line and not both. Finally, bus lines could also be disposed diagonally as illustrated in FIG. 16. These lines 76, 80 respectively run along two of the natural axes of the hexagonal array and would therefore simplify addressing of subelements.

The number of access switches and row bus lines is determined by the size constraints and the application. For the purpose of disclosing one exemplary non-limiting implementation (shown in FIG. 13), a single access switch 30 for each subelement 32 and four row bus lines 34a–34d for each row of the array will be assumed. The second type of switch is a matrix switch 36, which is used to connect a connection point 42 of one subelement (see FIG. 17) to the connection point of a neighboring subelement. This allows an acoustical subelement to be connected to a system channel through the integrated electronics associated with a neighboring acoustical subelement. This also means that an acoustical subelement may be connected to a system channel even though it is not directly connected via an access switch. While FIG. 13 shows three matrix switches per subelement, it is also possible to have fewer than three to conserve area or to allow for switches which have lower on resistance and therefore have larger area. In addition, matrix switches can be used to route around a known bad subelement for a given array. Finally, while hexagonal subelements are shown, rectangular subelements are also possible.

Figure 17:
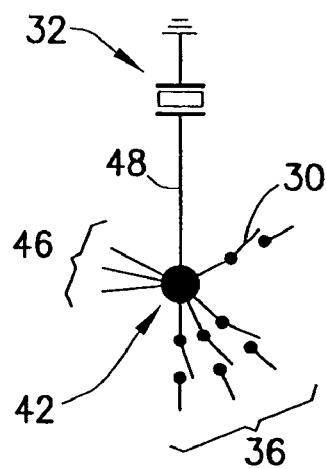
FIG. 17 is a drawing showing connections to a common connection point in the electronics associated with a particular acoustical subelement in accordance with the embodiment depicted in FIG. 13.

Referring to FIG. 17, each of the subelements is connected to a common connection point 42 in the electronics associated with the acoustical subelement 32. This common connection point 42 electrically connects eight components in each subelement. The common connection point 42 connects the acoustic subelement or transducer 32 to the access switch 30 for that subelement, to the three matrix switches 36 associated with that subelement, and to the three matrix switches associated with three neighboring subelements via connections 46. A signal that travels through a matrix switch gets connected to the common connection point of the neighboring subelement.

FIG. 13 depicts how the switching network might work for a particular subelement. This is only an exemplary arrangement. A bus 34, which contains four row bus lines 34a through 34d, runs down the row of subelements 32. FIG. 13 shows only three subelements in this row, but it should be understood that other subelements in this row are not shown. The row bus lines of bus 34 are multiplexed to system channel bus lines of system channel bus 38 at the end of a row by means of multiplexing switches 40, which form a cross-point switching matrix. As seen in FIG. 13, each row bus line 34a–34d can be connected to any one of the system channel bus lines of bus 38 by turning on the appropriate multiplexing switch 40 and turning off the multiplexing switches that connect the particular row bus line to the other system channel bus lines. These multiplexing electronics can be off to the side and thus are not as restricted by size. FIG. 13 shows a fully populated cross-point switch. However, in cases wherein it is not necessary to have switches that allow every bus line to be connected to every system channel, a sparse cross-point switch can be used in which only a small subset of the system channels can be connected to a given bus line, in which case only some of switches 40 depicted in FIG. 13 would be present.

An access switch is so named because it gives a subelement direct access to a bus line. In the exemplary implementation depicted in FIG. 13, there are six other switch connections for each subelement. These connections take the form of matrix switches 36. A matrix switch allows a subelement to be connected to a neighboring subelement. While there are six connections to neighboring subelements for each subelement in this hexagonal pattern, only three switches reside in each subelement while the other three connections are controlled by switches in the neighboring subelements. Thus there is a total of four switches and associated digital logic in each subelement. This is just one exemplary implementation. The number of bus lines, the number of access switches, and the number and topology of the matrix switches could all be different, but the general concept would remain.

Figure 18:
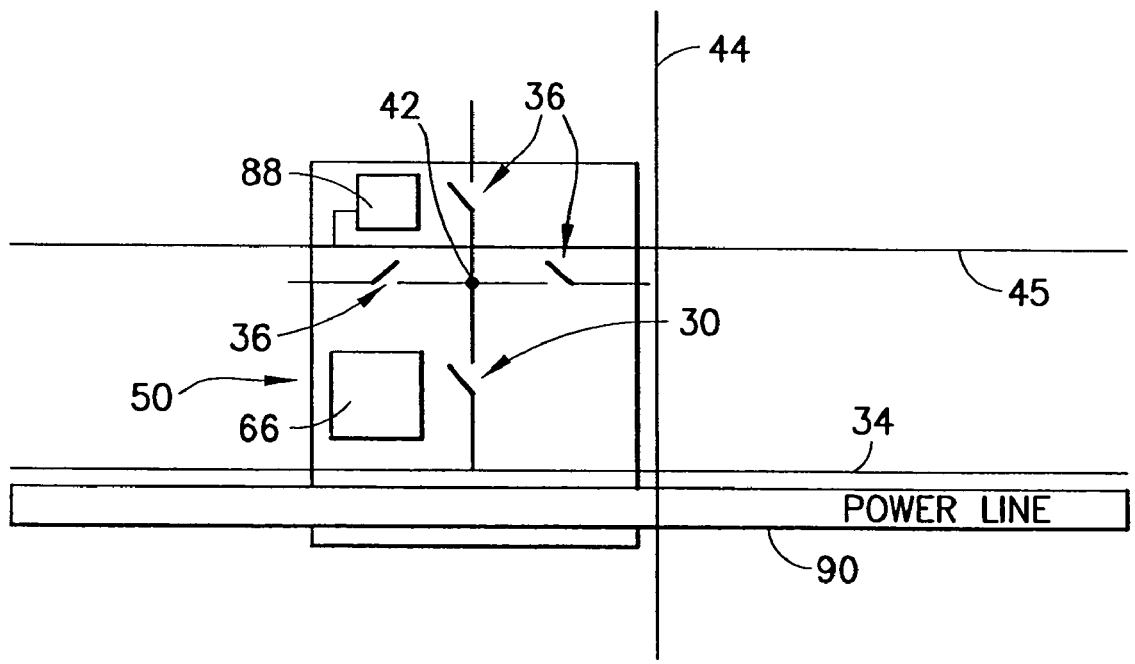
FIG. 18 is a drawing showing components of a representative unit switch cell built beneath and electrically connected to an acoustical subelement (not shown).

FIG. 18 shows some of the components of a representative unit switch cell built beneath and electrically connected (via connection point 42) to an acoustical subelement (not shown). The unit switch cell may be electrically coupled to the acoustical subelement via a metal pad 66 of the type depicted in FIG. 4. The unit switch cell comprises an access switch 30 that connects the connection point 42 to a bus line 34 and three matrix switches 36. These switches are of a type that have switch state memory for storing the current switch state. The unit switch cell further comprises latches 88 (only one of which is shown) for storing data representing the future switch states of the access switch 30 and the three matrix switches 36. The future switch state data is received via a digital data bus 45 comprising multiple bus lines (only one bus line being shown in FIG. 18). In response to a write signal received via a control bus 44 comprising multiple bus lines (again only one bus line is shown), the future switch state data on data bus 45 is written into the latches 88. In response to a read signal received via the control bus 44 during a subsequent cycle, the switch state data is read out from the latches and converted (by logic not shown) into control signals that will change the states of the switches accordingly. These new switch states will be stored in the switch state memories of the switches. The latch 88 and switches 30 and 36 receive voltage supplies via power line 90.

Although the access and matrix switches can be separately packaged components, it is possible to fabricate the switches within the same semiconductor substrate on which the MUT array is to be fabricated. These switches may comprise high-voltage switching circuits of the type disclosed in U.S. patent application Ser. No. 10/248,968 entitled "Integrated High-Voltage Switching Circuit for Ultrasound Transducer Array". Each switch comprises two DMOS FETs that are connected back to back (source nodes shorted together) to allow for bipolar operation. Current flows through the switch terminals whenever both FETs are turned on. The states of the switches are controlled by respective switch control circuits. The states of the switch control circuits are in turn dictated by outputs from a programming circuit, which programs the switch control circuits in accordance with an optimized switching configuration derived using the algorithm disclosed herein. A scan controller loads the optimized switching configuration into the programming circuit. Although use of CMOS high-voltage switches is one preferred embodiment, the invention described here is directly applicable to other switching technologies such as low voltage switches, MEMS switches and other future switch technologies in development.

Figure 19:
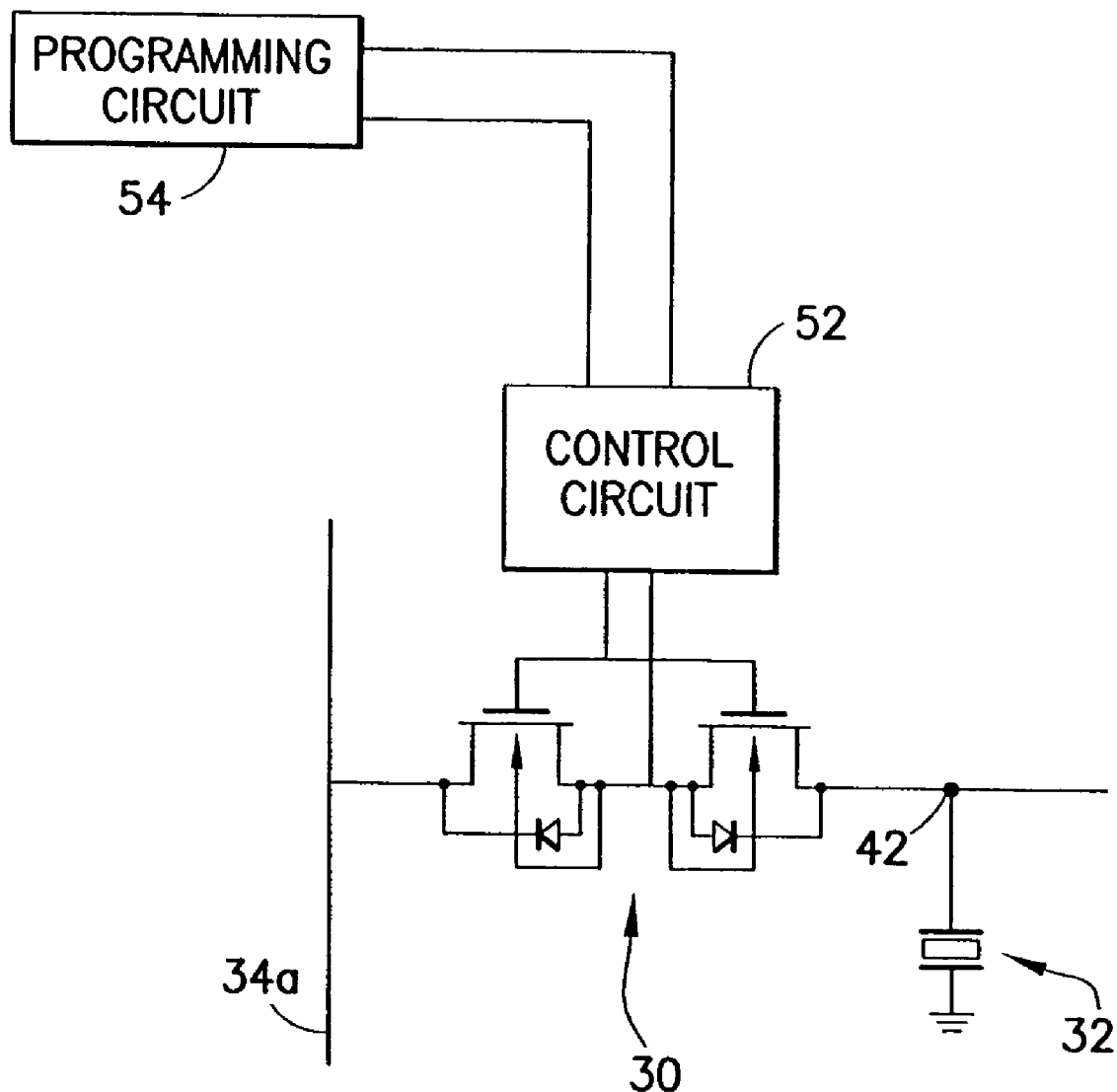
FIG. 19 is a drawing showing an access switch and circuitry for controlling the state of that access switch, as previously disclosed in U.S. patent application Ser. No. 10/248,968.

FIG. 19 shows an acoustical subelement 32 connected to an access switch 30 via a common connection point 42. The six other lines that connect to the connection point 42 are not shown. For this example, the access switch 30 comprises the aforementioned pair of back-to-back DMOS FETs. The control circuit 52 turns the switch 30 on or off as a function of control signals sent by the programming circuit 54. When access switch 30 is turned on, the acoustical subelement 32 (i.e., a subarray of interconnected cMUT cells) is connected to the row bus line 34a. For this configuration, the electronics associated with each acoustical subelement will comprise one access switch, three matrix switches, a respective control circuit for each of these four switches, and a respective conductor connecting the common connection point to the matrix switches of three neighboring subelements (not shown).

The signal that travels from the subelement to the row bus line is the electrical receive signal. Here the receive signal is the electrical response generated by the acoustical subelement when a sound pressure wave interacts with the transducer. The transmit signal, in which an electrical pulse is generated by the ultrasound system, travels from the row bus line to the matrix switch. For a given channel, this electrical excitation pulse travels through a system channel bus line to a row bus line. The signal travels from the row bus line to the acoustical subelement through an access switch and also travels to other subelements through the matrix switches.

The number of switches that fit behind an acoustical subelement is limited. The size of the switch determines the on resistance of the switch and the smaller the switch the larger the on resistance. The delay and distortion caused by the switching increases as the switch on resistance increases. This means that there is a tradeoff between the number of switches behind an acoustical subelement and the delay introduced by those switches. One solution to that tradeoff involves reducing the number of switches to a small number while retaining as much flexibility as possible. This reduction is achieved by using matrix switches to allow acoustic subelements to be attached to a system channel through other subelements, and by limiting the number of access switches to a small number.

The bus lines that connect the access switches to the system channels also take space in the electronics layer, so minimizing the number of bus lines is also beneficial. The number of unique channels that can be directly connected to acoustic subelements in the same row is determined by the number of bus lines. However, since the matrix switches allow subelements in one row to connect to subelements in other rows, the number of channels in a row is increased by the matrix switches. This allows the number of bus lines to be kept small, while still servicing a large number of channels. Of course, having more bus lines increases the flexibility but requires more space.

The use of matrix switches means that the number of access switches behind each subelement can be reduced. In the extreme case there is only one access switch for each subelement. However, if there is more than one bus line, a determination must be made as to which bus line each access switch should be connected. One solution is to stagger the connections so that the bus line connected to repeats every N subelements in a row, where N is a number determined by the requirement of minimum signal distortion as discussed below. Referring to FIG. 13, each subelement 32 in the row is connected to one of the row bus lines in the row bus 34 via a respective access switch 30. This pattern of staggered connections repeats every four subelements. The staggering allows more bus lines with fewer access switches and combined with the matrix switches, still allows for great flexibility as to which system channels can be connected to each subelement. Of course having more than one access switch per cell increases the flexibility of the connections but requires smaller switches with higher on resistance.

Figure 20:
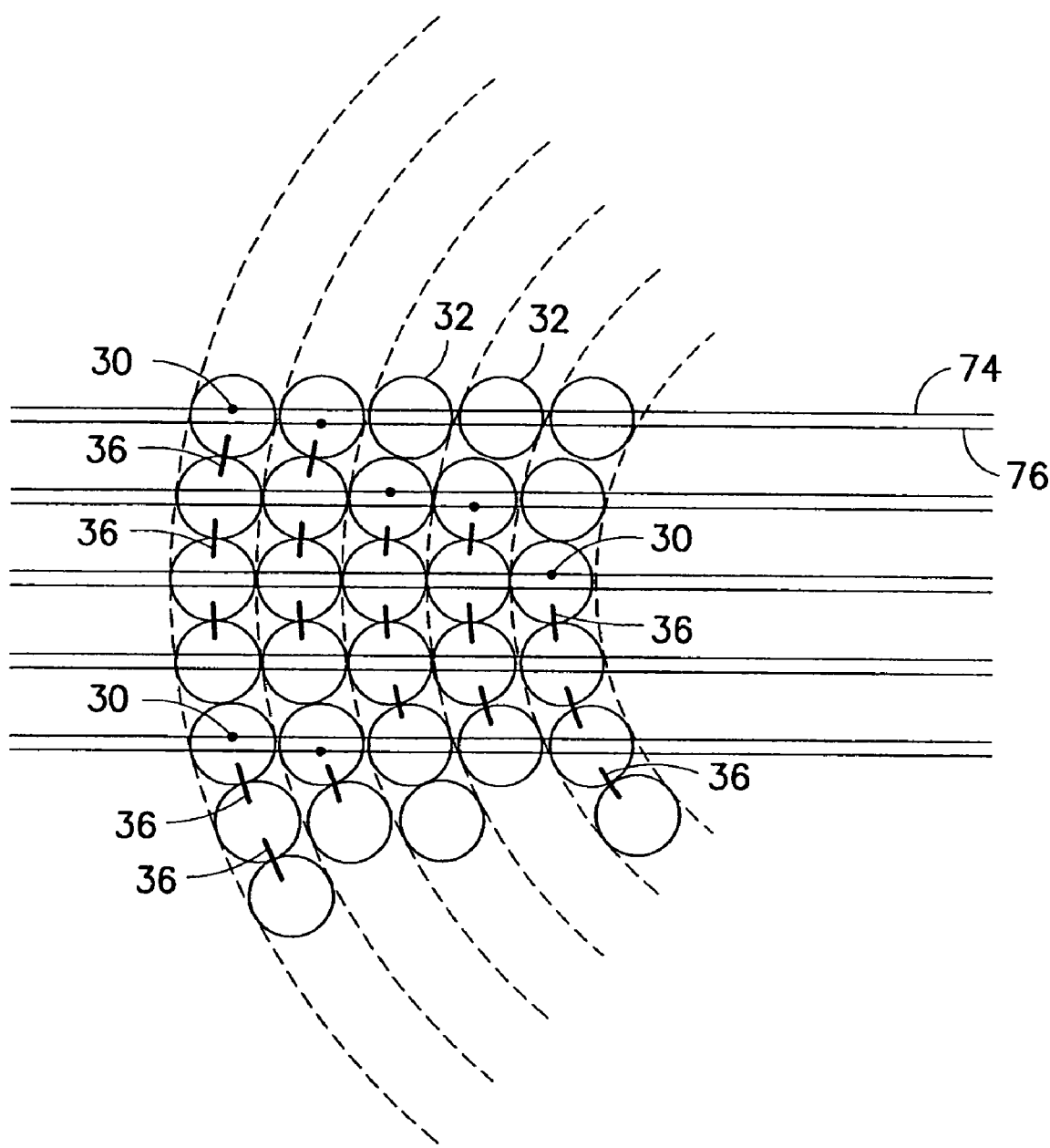
FIG. 20 is a drawing showing an arrangement of access and matrix switches for use with rings (portions of which are indicated by dashed arcs) with single subelement width are packed close together. Access switches are indicated by solid dots; matrix switches are indicated by dashes.

Generally, the number of rows N after which the pattern repeats is determined by the maximum number of matrix switches which can be strung together while still maintaining adequate signal integrity. This number comes out of the understanding that the matrix switch resistance and cMUT capacitances together form an RC delay line with a time constant of delay which varies exponentially with the number of series taps N. Staggering the access switches on multiple row bus lines allows the number of elements that can be supported to be increased given the constraint of the delay line. As illustrated in FIG. 20, the worst case for the design occurs where rings (portions of which are indicated by dashed arcs) with single subelement width are packed close together. The vertical sections of the ring provide the worst case since bus lines 74, 76 in this design run horizontally. In the horizontal sections of the rings, one could just use a single access switch at every subelement since they would all be the same as the bus lines run parallel to the rings. In the vertical sections however, every row of subelements 32 is associated with a different bus line that is connected to a different system channel. Therefore, subelements spaced vertically in this area can only be supported using matrix switches 36, represented by dashes. In FIG. 20, there are two bus lines per row, and the pattern of access switches 30 (represented by dots) repeats every four rows. At each row, two rings are supported by the two access switches and their associated string of subelements grouped with matrix switches. Since the pattern repeats after four rows, this particular architecture will support a maximum of 2×4=8 rings. In general for an array with M bus lines on each row and N taps for each string of subelements, a maximum of K system channels can be supported where K=M×N. Of course, most sections of the rings will be neither perfectly horizontal nor perfectly vertical. Therefore the task of the system designer is to optimize the array configuration at all points in the aperture under the constraints of the architecture.

For the particular implementation of the reconfigurability disclosed herein, there are limitations imposed by the electronics. There is a set of rules that governs the switching configurations for a system. In addition to the hard rules, there are the guiding principles such as reducing the distance between an acoustical subelement and a connection point. The rules must be obeyed and the guiding principles can be used to improve performance. The rules are as follows:

[1] Each row has "n" row bus lines. For the example disclosed herein, n=4. This means that for the entire row, there are only four system channel bus lines to which the access switches can connect.

[2] Each subelement in the row connects to only one of the n row bus lines. This follows from the fact that there is only a single access switch in the subelement. This also means that a given subelement can only be directly connected to a single system channel, with that channel being determined by the multiplexer between the system channel bus lines and the row bus lines.

[3] Each row bus line is connected to a single system channel bus line. While the system channel bus lines are multiplexed to the row bus lines, this connection cannot change for a given configuration.

[4] The pattern of which row bus line is connected to a given access switch repeats over the row. For the case described herein, the pattern repeats every four subelements.

[5] For a given circuit implementation, the total number of access switches connected to the same row bus line is a small finite number. In the particular case discussed later in this disclosure, the limit is four. This results from current draw limitations that are imposed by the limited size of the row bus lines. The limit is based on simulations and can be increased by increasing the size of the row bus lines, thus enabling larger current draws, but this might require larger subelements.

Determining the switching network configuration entails determining which access switches are on and how the multiplexer (meaning the bank of multiplexer switches 40 partly depicted in FIG. 13) between row bus lines and system channel bus lines is set. The matrix switch states are easy to determine, once the desired pattern is known. The matrix switches are set by simply determining if the neighboring subelement, to which the switch connects, should be on the same system channel or not. So the work is determining how to connect system channels to the multiplexed row bus lines. Once this is known, the access switches are also easy to assign.

To form a linear scan, the active aperture of the mosaic annular array must be stepped across the underlying two-dimensional array. This stepping requires that the switching network be reconfigured. There are several ways in which this stepping can be done. If the required beam spacing, as determined by the resolution of the array and the requirements of the application at hand, is such that stepping an entire subelement is acceptable, then the same algorithmically derived switch configuration can be used for each beam. In this case the switching configuration simply steps over one or several subelements for each beam. In order to minimize the reprogramming and power used by the system to reconfigure, it may be possible to transfer switch states directly from one subelement to the neighbor and thereby avoid reprogramming the entire array externally. However, in addition to translating the access and matrix switch pattern, the multiplexer connecting the row bus lines to the system channel bus lines must also be changed. When stepping the beam by entire subelements in the direction of the row bus lines, this change is simply a rotation of the channels. For example, if four system channels, designated A, B, C, and D respectively, are connected to the four row bus lines of a particular row for a particular configuration, when the switching pattern is scanned to the next beam location, the state of the system channel/row multiplexer must be adjusted so that the system channels rotate among the four row bus lines, e.g., system channels B, C, D, and A are connected in that order to the same four row bus lines respectively. Alternatively, rather than change the multiplexing between system channels and row bus lines, the system beamformer could take into account the change in geometry directly and therefore adjust the delays on the four channels to take into account the new delays.

As mentioned above, if the annular rings are stepped such that the motion is an integer multiple of the subelements there is no need to re-optimize for each beam (assuming that the underlying switch matrix has uniform electrical properties across the entire underlying two-dimensional array). However, there may be cases in which the desired beam density calls for lines to be closer together than a single subelement. In this case the beam center is stepped a fraction of a subelement, e.g., the aperture is deformed to effectively steer the beam a half step between full steps of the aperture, thereby increasing the resolution of the imager. For these cases the optimization does not simply translate and a new optimization must be run for each fractional step. However, these fractional stepping configurations may re-occur as the annular array is stepped across the underlying two-dimensional array to form a linear scan. In these cases, wherever the same fractional step is required, the optimization will be the same and can be re-used. So even in the case of fractional stepping, there will be a small number of optimizations required. In these cases, to save programming time and power consumption, it may be possible to fire all the beams for a particular configuration and step that configuration across the array at the coarse beam spacing. In this case it would be possible to pass configurations from subelement to neighbor directly. After the coarse scan has been completed, a new configuration which represents a fractional step from the old configuration can be programmed and stepped across the array. This can be repeated for each fractional step. The resulting coarsely spaced beams from each configuration can be interleaved by the scan converter to give the desired fine beam spacing. It should also be noted that when mixing beams from different configurations, it may be necessary to adjust the gain from beam to beam to compensate for beamforming gain differences and to blend the lines from those different configurations.

The foregoing aspects can be summarized as follows:

(a) When stepping integer numbers of subelements, switch states can be passed directly from subelement to neighbor without the need to program via the digital bus. This saves time and power.

(b) When stepping fractions of subelements, the beams for each different configuration can be stepped independently at the coarse beam spacing using the direct subelement to neighbor communication scheme and the resulting sets of course beams can be interleaved by the scan converter to get the full resolution.

(c) When stepping integer numbers of subelements, the multiplexer between row bus lines and system channels changes in a well-defined way, i.e., a rotation of the channels. This can simplify the control.

(d) When stepping integer numbers of subelements, it is not actually necessary to change the multiplexer between row bus lines and system channels. If the system beamformer is aware of the state, it can change the delays on the given channels to account for the new geometry. This, however, requires a more sophisticated system beamformer and does not allow these reconfigurable probes to operate on current machines.

The incorporation of access and matrix switches for connecting sensor elements to bus lines provides great flexibility. In accordance with various embodiments of the invention, one or more of the following features can be employed:

(1) The access switches can be staggered to reduce the number of access switches required for a given number of bus lines.

(2) A single access switch can be used for a subelement in a staggered pattern.

(3) A random ordering of access switch to bus line mapping can be employed to reduce artifacts due to the repeating patterns.

(4) More than one access switch can be used in each subelement, but still fewer than the number of bus lines and system channels.

(5) Bus lines can be connected to system channels using a cross-point switching matrix.

(6) A sparse cross-point switch can be used to connect bus lines to system channels.

(7) Switches can be configured to ensure that there is a respective different access switch connected at both ends of a long run of matrix switch connections, which access switches are connected to the same bus line, to reduce delay.

(8) Switching configurations can be employed in which there are a set of matrix switches and a limited number of access switches. The matrix switches connect neighboring subelements dynamically. The access switches connect to bus lines that are multiplexed to system channels.

In accordance with various embodiments of the invention, one or more of the following additional features can be present in the system:

(1) One access switch per bus line is used in each subelement.

(2) Multiple bus lines can be used per row.

(3) The bus lines can be disposed both vertically and horizontally within an array. In accordance with one embodiment, if one set of bus lines is disposed horizontally and another set is disposed vertically, each subelement or group of subelements will be connectable to a vertical bus line via one access switch and will further be connectable to a horizontal bus line via a different access switch. However, in the case where bus lines are run in both directions because the electronic real estate available for bus lines is running low and more bus lines are needed, but there is still only a single access switch in a subelement, then each subelement's access switch could be connected to either the horizontal bus line or the vertical bus line and not both. This also has implications when the number of switches that can be on for a given bus line is limited by current draw and the size of the line.

(4) Access switches can be chosen to lie equidistant from either edge of a ring (or other shape) to minimize delay inside the ring. An "edge of a ring" refers to the case in which the reconfigurability is used to approximate an annular array. In this case there is some desired annular array or ring structure that one wants to mimic by connecting subelements. The edge of the ring refers to the subelement near the border of the ring that one is trying to approximate, i.e., it is the edge of the larger element which is formed by connecting subelements. The access switches should be chosen to be on both sides of the element, not all on one side. The shape need not be a ring; instead other shapes could be used, and it would be best to have access switches on both edges of the shape that is approximated by connecting the subelements.

(5) More than one access switch per bus line could be used in each subelement. This redundant connection improves device yield.

(6) One could provide the ability to update ring patterns between transmit and receive and at multiple intervals during receive.

(7) A single access switch could be connected to an entire ring of subelements, each subelement in turn being connected together by matrix switches.

(8) Multiple access switches could be connected to an entire ring, with matrix switches between subelements having access switches to form respective sections of the ring.

(9) Multiple access switches could be connected to an entire ring, with the switches being distributed at equal distances spaced around the ring to reduce the signal delay for those subelements between switches

(10) Multiple rings can be formed, wherein each ring is connected to a single system channel using one or more access switches, each of which is connected to a bus line, which is in turn connected to a system channel.

(11) Multiple redundant matrix switch connections can be employed to form a single ring in order to reduce the series resistance and thereby reduce the delay.

(12) Matrix switches can be used to route around a known bad subelement for a given array.

(13) Patterns other than rings can be formed while still choosing access switch placement to minimize delay.

(14) An entire ring pattern can be translated to create a moving beam by repeated use of the minimum delay algorithm at each new step in the translation.

(15) The center of an element can be stepped by an increment less than a complete subelement by changing the shape of the element.

The switching electronics can be built using CMOS or BiCMOS, or SOI, or MEMS or other as yet unidentified switching technology.

While the invention has been described with reference to preferred embodiments, it will be understood by those skilled in the art that various changes may be made and equivalents may be substituted for elements thereof without departing from the scope of the invention. In addition, many modifications may be made to adapt a particular situation to the teachings of the invention without departing from the essential scope thereof. Therefore it is intended that the invention not be limited to the particular embodiment disclosed as the best mode contemplated for carrying out this invention, but that the invention will include all embodiments falling within the scope of the appended claims.

The invention claimed is:

1. A device comprising
a multiplicity of sensor elements arranged in rows;
a plurality of bus lines;
a plurality of system channels;
a multiplicity of multiplexer switches for selectively connecting various bus lines to various system channels;
a first set of access switches for selectively connecting a first set of said sensor elements in a first row to a first bus line of said plurality of bus lines, each access switch of said first set of access switches being disposed underneath a respective sensor element of said first set of sensor elements, a first access switch of said first set of access switches being connected to a first sensor element that is a member of said first set of sensor elements;

a multiplicity of sets of matrix switches, each of said sets of matrix switches selectively connecting a respective sensor element of said multiplicity of sensor elements to a respective set of adjacent sensor elements, a first matrix switch of said multiplicity of sets of matrix switches being connected to said first sensor element and to a second sensor element that is not a member of said first set of sensor elements; and control circuitry that controls said multiplexer switches, said access switches and said matrix switches in accordance with a selected switching configuration such that said first sensor element is connected to a first system channel via a first multiplexer switch of said multiplicity of multiplexer switches that is connected to said first bus line, via said first bus line, and via said first access switch, while at the same time said second sensor element is connected to said first access switch via said first matrix switch.

2. The device as recited in claim 1, further comprising a second set of access switches for selectively connecting a second set of said sensor elements in said first row to a second bus line of said plurality of bus lines, each access switch of said second set of access switches being disposed underneath a respective sensor element of said second set of sensor elements, a second access switch of said second set of access switches being connected to and disposed under a third sensor element that is a member of said second set of sensor elements, a second matrix switch of said multiplicity of sets of matrix switches being connected to said third sensor element and to a fourth sensor element that is not a member of said second set of sensor elements, wherein said control circuitry controls said multiplexer switches, said access switches and said matrix switches in accordance with said selected switching configuration such that said third sensor element is connected to a second system channel via a second multiplexer switch of said multiplicity of multiplexer switches that is connected to said second bus line, via said second bus line, and via said second access switch, while at the same time said fourth sensor element is connected to said second access switch via said second matrix switch.

3. The device as recited in claim 1, further comprising a second set of access switches for selectively connecting a second set of said sensor elements in said first row to said first bus line, each access switch of said second set of access switches being disposed underneath a respective sensor element of said second set of sensor elements, a second access switch of said second set of access switches being connected to and disposed under a third sensor element that is a member of said second set of sensor elements, a second matrix switch of said multiplicity of sets of matrix switches being connected to said third sensor element and to a fourth sensor element that is not a member of said second set of sensor elements, wherein said control circuitry controls said multiplexer switches, said access switches and said matrix switches in accordance with said selected switching configuration such that said third sensor element is connected to said first system channel via a second multiplexer switch of said multiplicity of multiplexer switches that is connected to said first bus line, via said first bus line, and via said second access switch, while at the same time said fourth sensor element is connected to said second access switch via said second matrix switch.

4. The device as recited in claim 1, wherein each of said sensor elements comprises a respective multiplicity of micromachined ultrasound transducer (MUT) cells, and each MUT cell comprising a top electrode and a bottom electrode, wherein the top electrodes of the MUT cells making up any particular subelement are connected together and are not switchably disconnectable from each other, and the bottom electrodes of those same MUT cells are connected together and are not switchably disconnectable from each other.

5. The device as recited in claim 1, further comprising a semiconductor substrate, said access switches and said matrix switches being fabricated in or on said semiconductor substrate and said sensor elements being fabricated in or on said semiconductor substrate.

6. The device as recited in claim 1, further comprising first and second substrates laminated together, said access switches and said matrix switches being fabricated in or on said first substrate and said sensor elements being fabricated in or on said second substrate.

7. The device as recited in claim 1, wherein said control circuitry controls said switches so that the aperture on transmit is different than the aperture on receive.

8. The device as recited in claim 1, wherein said control circuitry controls said switches so that switched-on sensor elements form a generally annular ring.

9. The device as recited in claim 2, wherein said access switches of said first and second sets of access switches are staggered to reduce the number of access switches required for a given number of bus lines.

10. The device as recited in claim 2, wherein each sensor element in said first row has only one respective access switch associated therewith, each of said access switches being connected to only one respective bus line of a set of bus lines associated with said first row of sensor elements.

11. The device as recited in claim 10, wherein a random ordering of access switch-to-bus line mapping is used to reduce artifacts due to repeating patterns.

12. The device as recited in claim 2, wherein each sensor element in said first row has a respective set of N access switches associated therewith, the access switches of said set being connected to respective bus lines of a set of bus lines associated with said first row of sensor elements, wherein the number of bus lines in said set of bus lines associated with said first row of sensor elements is greater than or equal to N.

13. The device as recited in claim 1, wherein said multiplexer switches form a cross-point switching matrix whereby each bus line can be selectively connected to each system channel.

14. The device as recited in claim 1, wherein said multiplexer switches form a sparse cross-point switching matrix.

15. The device as recited in claim 1, wherein said control circuitry controls said access and matrix switches to ensure that there is a respective different access switch connected at both ends of a long run of matrix switch connections, which access switches are connected to the same bus line, to reduce delay.

16. The device as recited in claim 1, wherein said plurality of bus lines comprises a set of horizontal bus lines and a set of vertical bus lines.

17. The device as recited in claim 1, wherein said control circuitry controls said access switches so that access switches are chosen to lie equidistant from either edge of a ring (or other shape) formed by selected sensor elements to minimize delay inside said ring (or other shape).

18. The device as recited in claim 1, wherein more than one access switch per bus line is used in each sensor element to provide a redundant connection to improve yield.

19. The device as recited in claim 1, wherein said control circuitry controls said switches so that the aperture is different at multiple intervals during receive.

20. The device as recited in claim 1, wherein said control circuitry controls said switches so that a single access switch is connected to an entire ring of sensor elements, each sensor element in said ring in turn being connected together by matrix switches.

21. The device as recited in claim 1, wherein said control circuitry controls said switches so that multiple access switches are connected to an entire ring of sensor elements, with matrix switches between sensor elements having access switches to form respective sections of said ring.

22. The device as recited in claim 1, wherein said control circuitry controls said switches so that multiple access switches are connected to an entire ring of sensor elements, with said access switches being distributed at equal distances spaced around said ring to reduce the signal delay for those sensor elements between access switches.

23. The device as recited in claim 1, wherein said control circuitry controls said switches so that multiple rings of sensor elements are formed, wherein each ring is connected to a single system channel using one or more access switches, each of which is connected to a bus line, which is in turn connected to a system channel.

24. The device as recited in claim 1, wherein said control circuitry controls said switches so that multiple redundant matrix switch connections are employed to form a single ring in order to reduce the series resistance and thereby reduce the delay.

25. The device as recited in claim 1, wherein said control circuitry controls said switches so that selected matrix switches are used to route around a known bad sensor element.

26. The device as recited in claim 1, wherein said control circuitry controls said switches so that switched-on sensor elements form patterns other than rings while still choosing access switch placement to minimize delay.

27. The device as recited in claim 1, wherein said control circuitry controls said switches so that an entire ring pattern of sensor elements can be translated to create a moving beam by repeated use of a minimum delay algorithm at each new step in the translation.

28. The device as recited in claim 1, wherein said control circuitry controls said switches so that the center of an element can be stepped by an increment less than a complete subelement by changing the shape of the element.

29. The device as recited in claim 1, wherein said control circuitry controls said switches so that when stepping integer numbers of subelements, switch states can be passed directly from subelement to neighbor without the need to program via the bus lines.

30. The device as recited in claim 1, further comprising a scan converter, wherein said control circuitry controls said switches so that when stepping fractions of subelements, the beams for each different configuration can be stepped independently at the coarse beam spacing using the direct subelement to neighbor communication scheme and the resulting sets of course beams can be interleaved by said scan converter to get the full resolution.

31. The device as recited in claim 1, wherein said control circuitry controls said switches so that when stepping integer numbers of subelements, the multiplexer switches between row bus lines and system channels change by a rotation of the channels.

32. The device as recited in claim 1, further comprising a system beamformer, wherein said control circuitry controls said switches so that when stepping integer numbers of subelements, the states of the multiplexer switches between row bus lines and system channels, but rather said system beamformer changes the delays on the given channels to account for said stepping.

33. An ultrasound transducer array comprising:
a multiplicity of bus lines;
a multiplicity of access switches, each access switch being connected to one of said bus lines; and
a multiplicity of subelements, each subelement being switchably connectable to one of said bus lines via a respective one of said access switches and comprising a respective multiplicity of MUT cells and a respective plurality of matrix switches, and each MUT cell within a particular subelement being connected together and not switchably disconnectable,
wherein each subelement is switchably connectable to each adjacent subelement via a respective matrix switch.

34. The array as recited in claim 33, wherein a selected subelement can be switchably connected to a selected bus line via a matrix switch that connects said selected subelement to a neighboring subelement and via the access switch via which neighboring subelement is connected to said selected bus line.

35. The array as recited in claim 33, further comprising programming means for interconnecting selected subelements to form respective elements.

36. The array as recited in claim 35, wherein said respective elements form multiple concentric annuli of an electronically formed annular array.

37. The array as recited in claim 36, wherein said electronically formed annular array is moved, under electronic control, across said transducer array.

38. A device comprising
a multiplicity of sensor elements;
a plurality of bus lines;
a first set of access switches for selectively connecting a first set of said sensor elements in a first row to a first bus line of said plurality of bus lines, a first access switch of said first set of access switches being connected to a first sensor element that is a member of said first set of sensor elements;
a multiplicity of sets of matrix switches, each of said sets of matrix switches selectively connecting a respective sensor element of said multiplicity of sensor elements to a respective set of adjacent sensor elements, a first matrix switch of said multiplicity of sets of matrix switches being connected to said first sensor element and to a second sensor element that is not a member of said first set of sensor elements; and
control circuitry that controls said access switches and said matrix switches in accordance with a selected switching configuration such that said first sensor element is connected to said first bus line via said first access switch, while at the same time said second sensor element is connected to said first access switch via said first matrix switch.

39. The device as recited in claim 38, wherein each of said sensor elements comprises a respective multiplicity of micromachined ultrasound transducer (MUT) cells, and each MUT cell comprising a top electrode and a bottom electrode, wherein the top electrodes of the MUT cells making up any particular subelement are connected together and are not switchably disconnectable from each other, and the bottom electrodes of those same MUT cells are connected together and are not switchably disconnectable from each other.

* * * * *